United States Patent [19]
Erickson

[11] Patent Number: 5,524,637
[45] Date of Patent: Jun. 11, 1996

[54] INTERACTIVE SYSTEM FOR MEASURING PHYSIOLOGICAL EXERTION

[76] Inventor: Jon W. Erickson, 3406 Rambow Dr., Palo Alto, Calif. 94306

[21] Appl. No.: 267,671

[22] Filed: Jun. 29, 1994

[51] Int. Cl.⁶ .................................................. A61B 5/103
[52] U.S. Cl. ................... 128/779; 482/8; 482/900
[58] Field of Search ..................... 128/774, 779, 128/782; 33/511, 512; 482/8, 900, 902

[56] References Cited

U.S. PATENT DOCUMENTS

| | | | |
|---|---|---|---|
| 4,416,293 | 11/1983 | Anderson et al. | 128/779 |
| 4,774,679 | 9/1988 | Carlin | 128/779 |
| 4,813,436 | 3/1989 | Au | 128/779 |
| 5,042,504 | 8/1991 | Huberti | 128/779 |
| 5,323,650 | 6/1994 | Fullen et al. | 128/779 |
| 5,357,696 | 10/1994 | Gray et al. | 128/779 |

Primary Examiner—Max Hindenburg
Attorney, Agent, or Firm—James Leary

[57] ABSTRACT

A system is provided for monitoring the physiological exertion of a user. One or more sensors are attached to the limbs of the user to measure the user's motion. The sensors can measure either the acceleration or the force on the limbs. The measured signal is transmitted to a monitor by a wireless transmitter, such as an infrared, acoustic or radio transmitter. The monitor determines and displays the level of physiological exertion of the user by a mathematical formula or a look up table based on the measured motion of the user. The system can also measure and display various other physiological parameters of the user, such as pulse rate, blood pressure, etc. The system includes an interactive video display with a branching video sequence. The rate of progress and the direction of the video sequence at each of the branching points are interactively controlled by the level of physiological exertion and the movements of the user. The system can also record and display the level of physiological exertion and other physiological parameters of the user over time to create a personal exercise log.

22 Claims, 4 Drawing Sheets

INTERACTIVE SYSTEM FOR MEASURING PHYSIOLOGICAL EXERTION

BACKGROUND OF THE INVENTION

1. Field of the Invention

The present invention relates to exercise equipment, physical training, and the accurate measurement of exertion. In particular, the present invention defines a system for conveniently monitoring the exertions of an individual performing exercise such as calisthenics. A primary objective of the present invention is to provide an accurate, inexpensive, and versatile system for monitoring exercise and estimating exertion, which can in turn be linked to video and multimedia equipment (such as are provided by many desktop computer systems) for simultaneous interactive education, training, entertainment, or other purposes.

2. Description of Background Art

The present invention concerns a novel design for an interactive exercise system, in which physiological exertion can be conveniently and automatically estimated by monitoring a course of exercise such as calisthenics, a training program, or walking or running in place. In brief, the motion of a subject (especially in a confined area) is monitored by one or more of several means, and used to estimate exertion by means of a reference table, matrix, flowchart, formula, or other expression of an algorithm. The algorithm may include such data as height, weight, age, gender, stride length, or other easily obtained numbers (shoe size, inseam length, sleeve length, and so on) which may conveniently increase the accuracy of the estimate or substitute for other data that are inconvenient to obtain. Perturbations to normal conditions, such as weights strapped to the legs or arms for physical training, could also be entered in such a table or formula to provide modified estimates of exertion.

The motion of the entire body, or of one or more limbs, may be monitored by any of several means. (The simplest means of course would be to generate a timing signal, such as a sound or visual cue, and rely on the individual to keep pace—this is essentially the approach taken by commercially available exercise videotapes!) One means would be to use an accelerometer sensor may be strapped to an ankle or wrist, and values may be relayed to a computer by means of acoustic, optical, or radio signals. A second means would be to strap a pressure sensor to the bottom of the subject's shoe, and relay such signals. A third means would be to monitor body and limb motion by means of a video camera, if necessary strapping one or more light-emitting diodes to a foot or hand to more clearly delineate the motion. The frequency or rate of body and limb motion could then be easily determined by evaluating individual pixels, applying any one of a number of algorithms such as edge detection, Fourier analysis, or best-fit criteria using simulations with one or more independent parameters. A fourth robust and inexpensive means of monitoring exertion would be by means of a low platform made up of two thin steel plates (e.g. 2 feet square and 0.25" thick), separated by pressure gauges (e.g. piezoelectric transducers) which transmit the impact forces on the plates when the subject walks or runs in place on the platform.

The invention is described as an "interactive" exertion measurement system because it can easily be linked to a video display which shows a sequence of video images corresponding to that seen during a walk or run through scenery of interest to the individual. The rate at which progress is made through such scenery could be related to the rate of motion of the legs and stride length. In a similar way, arm motions could be related to other video events.

Other kinds of information may also be monitored automatically, such as heart rate which can be easily measured by acoustic or infrared methods, using a device in contact with body. Thus an individual could use this system to maintain an exercise record, pursue a physical training program, and monitor improvements in cardiovascular fitness over time. In addition, a physician might use the present system, as an alternative or in preference to a mechanical treadmill, in standardized tests of cardiovascular fitness.

The background art involves several distinct disciplines. Automated or mechanical exercise equipment comes in a variety of forms including treadmills, stationary bicycles, and so forth. Some commercial treadmills are equipped with video equipment in order to provide a more esthetic or entertaining exercise experience. The chief purpose served by such equipment (other than cultural or social purposes familiar to anthropologists, such as displays of conspicuous consumption) is to provide a consistent and reproducible measure of exertion, along with some entertainment. The present invention achieves the same ends for calisthenics. Accelerometers, pressure gauges, and video motion detectors are in common use and under constant development for industrial, commercial, and scientific purposes. The wireless transfer of information by acoustic, optical, or radio methods is commonplace. For example, infrared pulses are employed by remote controls for home entertainment equipment and other consumer electronics (televisions, video tape recorders, telephone answering machines, and so on). Interactive video systems which use random-access video disks have been available commercially for over ten years, and have come into widespread use with the advent of CD-ROM (compact-disk-read-only-memory) players for home computers. The software and hardware necessary to embody the present invention is readily available. Biomechanics and kinesiology involve the study of body motions, exertion, and the efficiency with which various activities can be accomplished. Such activities may include walking, running, jumping, climbing stairs, skiing, and various sports.

The present invention is intended to provide a cost-effective, light-weight, and accurate system for monitoring physiological exertion. The design makes use of modern computer hardware and software, in order to provide the most accurate information at the least cost. The system may be used to provide interactive video entertainment as well.

SUMMARY OF THE INVENTION

In accordance with the present invention, a monitoring system is provided that offers accurate measurement of physiological exertion with interactive video capabilities, at relatively low cost. The system comprises a measuring device, wireless transmission of information, and associated computer hardware and software. The measuring device monitors the motion of the entire individual, or of one or more limbs.

In the illustrative embodiments, an accelerometer or pressure sensor is usually depicted. These sensors measure the forces exerted by the limb or body, which may result in a change in the velocity of a limb or which may be opposed by an equal and opposite force (e.g. the subject may press both hands against each other). Due to rapid development and decreasing prices in the field of micromachine technology, such miniature sensors will probably be the most economical and robust choice of measurement device. The wireless communication usually depicted is infrared light, for similar reasons of economy and robust practicality.

Identification and refinement of the algorithms: Identifying the particular algorithms that are most suitable to estimating the most common or important forms of exertion is relatively easily accomplished. Most physiological exertion involves applying force against resistance, but this may be in the form of muscle viscosity or the inertia of body levers, so little external work is accomplished and the rate of energy expenditure cannot be easily estimated. However, the level of physiological exertion can be directly measured by monitoring oxygen consumption, and this can be correlated with the parameters of motion for individual subjects engaged in a given activity. Walking, running, and other activities have been correlated with exertion level in this manner, and variations with different individuals in the general population have also been studied. (For more complex activities, it may be necessary to correlate the output of several sensors with the level of exertion, by means of neural net software or mathematical techniques of multivariate calibration.)

The refinement of a basic algorithm (which may take the form of a flowchart, formula, matrix, or table) for calculating a level of physiological exertion involves first determining the model or set of factors that best relates the motion of a subject with reference data. Then this calibration algorithm must be validated in practice, to ensure that it is robust and not sensitive to noise or irrelevant information, and that it successfully deals with individual variations for the normal demographic range (95%) in the target population Measurement of physiological exertion: The most accurate measurement of exertion in terms of calories burned is obtained by monitoring the rate of oxygen uptake and carbon dioxide output, or respiratory exchange. Although some oxygen debt can be incurred in the early stages of exercise (e.g. the first two minutes or so), eventually this oxygen debt is repaid and so the net oxygen consumption serves as an accurate measure of exertion.

However it seems impractical and inconvenient to measure respiratory exchange in most cases. A simpler approach is to calculate the exertion level for an average person at different performance levels in a given activity, and the adjustments or corrections corresponding to deviations from the average in the most significant physiological parameters. The most significant parameters in most cases will be those affecting biomechanical efficiency and energy: in particular weight, height, age, gender, and conditioning or training. Conditioning or training not only affects the cardiovascular and muscular efficiency of the body (as does a medical condition such as obesity), but may affect the choice of gait or technique. Other optional parameters may be adjusted to simulate different environmental conditions such as slippery ground, uphill motion, a strong headwind, and so on.

The general approach to identifying the appropriate algorithm is to begin with the average performance and the statistical mean, and then identify (1) the most significant functional or performance parameters of motion necessary to calculate the exertion level, and (2) the most significant demographic parameters for deviations in exertion level from the mean. This general approach can be followed for different populations and various different activities.

As noted, an oxygen debt is incurred in the first two minutes of exercise, until the cardiovascular system increases its steady state level to compensate. This higher steady state level has an upper limit, so that exertion levels above about 700 kilocalories per hour are not sustainable by most people. It is true that champion marathon runners can maintain exertion levels of about 1300 kilocalories per hour for over 2 hours, running at just over 11 miles per hour. However, individual variations will be much more pronounced for highly stressful activities. While the accuracy of the present approach may be refined and its scope may be extended, with sufficient statistical data for particular exertion levels and activities, generalizations may not be useful if individual variations are large.

Biomechanical estimates for walking and running: A relatively simple formula has been suggested for estimating the exertion in walking or running. The weight of the individual in pounds multiplied by the distance in miles and a coefficient of 0.56 (or the weight in kilograms times the distance in kilometers and a coefficient of 0.77) gives a reasonable estimate of the number of kilocalories used or energy exerted.

For purposes of comparison, typically 110 kilocalories per hour are burned in basal metabolism while simply standing still. The absolute exertion rates are about 170 kcal/hour at 2 mph, 210 at 2.3 mph, 290 at 3.5 mph, 380 at 4 mph, and 470 at 4.6 mph. About 650 kcal/hour are required when walking at about 5 miles per hour, and most people must run in order to exceed 5 miles per hour. Note that the energy expenditure per mile is remarkably constant for the average man: about 90 kcal/mile are required at 2.3 mph; 85 kcal/mile at 3.5 mph; and 100 kcal/mile at 4.6 mph.

The functional parameters of motion in walking and running deserve closer scrutiny. The energy expended per mile or per hour actually varies non-linearly with the rate of progress. The most efficient rate of walking is about 2 to 3.5 miles per hour, slightly faster for men and slightly slower for women. The average person is assumed to be a 155 pound, 5'8" tall, 25-year-old male with little training and a step length of about 2' or 0.6 meter. The basal metabolism while standing still is about 1.3 kilocalories per minute. At about 4 or 5 miles per hour, it becomes more efficient to run than to walk. Up to about 10 miles per hour, about 50% more exertion is required per mile for running. (From 10–20 mph, exertion levels of 1000–10,000 kcal/hour are required. But most people cannot sustain exertion levels above 700 kcal/hour for long periods of time so these high exertion levels are not considered here.)

Consider the most significant demographic parameters:

1. Height. Within limits, adjustments in stride length compensate for differences in height. Thus short and tall people walk with about the same expenditure of energy. Longer strides may require more energy, but fewer strides are needed to travel a given distance.

2. Weight. The energy expenditure per unit weight is nearly constant for walking horizontally or up a grade. Thus it is also possible to calculate in a simple manner the exertion necessary to walk while carrying a load up to about 30% of an individual's body weight. However, obesity introduces a kind of de-conditioning or inefficiency which can increase the necessary exertion by as much as 20%, over and above that associated simply with the weight. Reference must be made to standard tables of height and weight, to determine the likelihood of obesity.

3. Age. Biomechanical efficiency varies with age, for men from about 16% at 17 years of age to a peak of about 24% at 44 years of age, and thereafter declining.

4. Gender. Men tend to be slightly more efficient than women (about 10%).

5. Conditioning and training. Training can increase efficiency by 25% or so. Extremely fit individuals may be up to 100% more efficient than those out of condition. Training in a particular activity increases efficiency—for example, an experienced woodcutter may use about one third as much energy as does an untrained individual, in cutting the same amount of wood.

Environmental conditions are also quite significant. A slippery surface can increase the necessary level of exertion by as much as 80%. In still air, wind resistance contributes up to 5% of the total exertion at a 20 mile-per-hour sprint, and gale-force headwinds or tailwinds will alter the exertion levels. The grade of the surface or road (uphill or downhill) also alters the level of exertion necessary to travel a given distance.

Walking and running in place:. Any type of locomotion which minimizes raising the body or its parts will tend to be more efficient. Typically vertical motion accounts for only about 20% of energy expenditure at medium speeds of walking, and about 10% at rapid speeds. In contrast, walking or running in place must necessarily emphasize raising and lowering the body or its parts. Thus, the biomechanics for walking and running in place necessarily differ somewhat from that for forward locomotion.

The input data should include steps per minute and the height of the steps. A roughly linear correspondence will be assumed to exist between the step height when walking in place, and the step length when walking for true locomotion.

The algorithm for waling and running place: The exertion level is calculated for an individual in the normal range, and under normal conditions, using a flowchart described below. An equivalent algorithm might be expressed in the form of a formula, matrix, table, or by other means. An estimate that is within 15% accurate for 95% of the population will be acceptable. (Estimates of exertion for individuals using treadmills and exercise equipment are necessarily affected by the same physiological variations dealt with in the present algorithm.)

The demographic distributions of height, weight, and other characteristics of a given target population may shift over time. Moreover, the particular distributions may change from one population to another (e.g. the Japanese, American, and European markets will differ). Thus, the particular coefficients will have to be adjusted or tailored to a particular population.

To begin, multiply the step height by a coefficient of 5 to obtain the stride length, and divide by the stepping rate to calculate the equivalent rate of locomotion or effective speed. (This coefficient may be modified to take into account footwear, changes in demographics, and so on.)

1. Obtain the weight of the individual (e.g. by keyboard entry). In order to estimate the rate of exertion, multiply the weight times 0.56 times the effective speed.

2. Obtain the height of the individual. The individual height is significant, as are gender and age, in checking against standard tables of height and weight for excessive weight or obesity, or unusual thinness. A 20% increase in exertion rate is added for obesity. The correction factor for unusual thinness is not known, and a useful value may not in general exist due to the wide range of possible causes and associated pathologies.

(Minor alterations in the most efficient step rate and width are correlated with different heights. For the most part, a taller person will take fewer and longer steps than a short person, so that both travel at similar rates with similar exertion levels.)

3. Obtain the age of the individual. The efficiency or rate of locomotion for a given exertion level seems to reach a maximum at about age 44. In lieu of more precise information, add 1% for every year younger or older than 44, up to 30%.

(Percentile rankings of normal height and weight for a recent American population survey are:

| Percentile | Women | | Men | |
| --- | --- | --- | --- | --- |
| | Ht. (") | Wt. (lb.) | Ht. (") | Wt. (lb.) |
| 5% | 60 | 97–128 | 65 | 114–150 |
| 10% | 61 | 101–132 | 66 | 118–150 |
| 25–75% | 63–66 | 112–138 | 68–71 | 122–179 |
| 90% | 67 | 121–159 | 73 | 144–189 |
| 95% | 68 | 125–164 | 74 | 148–195 |
| | | | 75 | 152–200 |
| | | | 76 | 156–205 |
| | | | 77 | 160–211 |
| | | | 78 | 164–216 |

Roughly a 10% increase in average weight occurs from 25 to 35 years of age, for a given height and gender.)

4. Obtain the gender of the individual. The exertion level for a given rate of locomotion will be about 10% higher for women, than for men.

5. Obtain an estimate of the training or condition of the individual. This is necessarily qualitative, but may be made more meaningful by comparisons. Three levels of training may be clearly differentiated: little to no training, good training (amateur athlete, requiring daily exercise), and superb training (professional athlete). The exertion rate for a given rate of locomotion will decrease by about 25% for someone in good training, and about 35% for someone in superb training.

Various environmental options may be selected by the individual, either to represent actual conditions or if a "virtual reality" simulation is being depicted for entertainment purposes. For example, the grade of the surface underfoot, the traction, any loads being carried (up to 25% of body weight), the direction and strength of the wind, and other environmental conditions may be chosen.

6. The load being carried can be factored directly into the weight of the individual, up to about 25% of the body weight.

7. The grade directly influences the exertion level, or conversely determines the rate of locomotion for a specified exertion level. A 5.5 degree grade increases the exertion rate about 53% from 85 kcal/mile to about 130, and a 8.5 degree grade increases it by about 88% to about 160.

8. A slippery or low-traction surface underfoot may increase the exertion level for a given rate of locomotion by as much as 70%. For example, walking on a slippery floor, in dry sand, in powdery snow, or on ice requires more exertion for a given rate of forward locomotion.

9. Very windy conditions can significantly increase or decrease the exertion required for forward locomotion. Air resistance in the absence of wind contributes only a very small fraction to exertion, about 3% at high running speeds of about 15–20 miles per hour (at which the exertion rates can be 3000 to 10,000 kcal/hr). But the additional exertion necessary to work against a gale force headwind can be significant and may be estimated by multiplying the distance traveled and the force of the wind. Note that the force of the wind increases with the square of its speed, and varies with the cross-sectional area of the individual. For example, a 40–60 mph wind may exert a horizontal force on an individual that has an effect on exertion similar to an 8.5 degree grade.

Scope and limits of the present method: In clinical, commercial, and home applications the present invention will work best within strict boundary conditions. A robust monitoring system should be able to detect when boundary conditions have been violated, but it is important for those using the invention to simply recognize and understand the implicit assumptions and the limitations of the approach. Within quite wide boundary conditions, and for most people, the estimates of exertion will be quite accurate. Estimates may be made by algorithms constructed in like manner for other activities such as swimming, skiing, and so on, monitoring the acceleration and motion of the body and its parts.

A more detailed explanation of the invention is provided in the following descriptions and claims, and is illustrated in the accompanying drawings.

DESCRIPTION OF THE PREFERRED EMBODIMENTS

Figure 1:
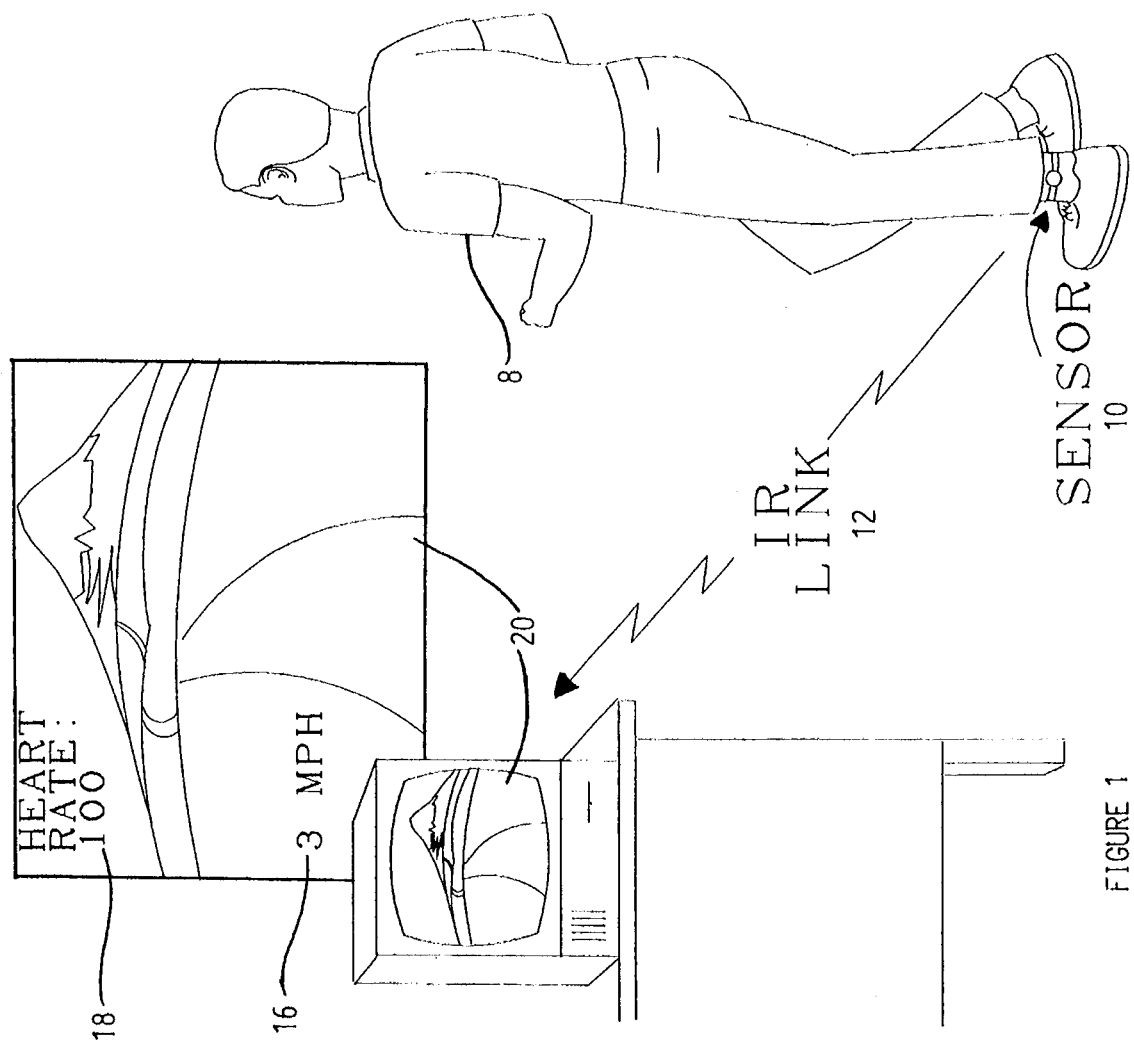
FIG. 1 shows how an individual may use the present invention to monitor the exertion level associated with running or walking in place.

FIG. 1 shows how an individual may use the present invention to monitor the exertion level associated with running or walking in place. The components of the invention are lightweight and compact, so that a practical embodiment may be quite portable. A medical office application is shown in this embodiment.

A user 8 of the system is seen running in place in FIG. 1. At least one sensor 10 is attached to the user 8 at an appropriate part of the user's anatomy, such as the sensor 10 attached to the user's ankle. The sensor 10 can include an accelerometer, a pressure sensor, a blood pressure sensor, a pulse rate detector or other types of sensing mechanisms. If desired, multiple sensors 10 can be used. The number of sensors necessary for physiological monitoring depends on the complexity of the exercise to be performed and the accuracy desired for the monitoring function. For simple, repetitive exercises, such as running in place, a single ankle sensor may provide a good enough correlation to physiological exertion for normal monitoring purposes. For more complex or varied exercises, it may be necessary to attach a monitor to each of the user's limbs to monitor arm and leg motion, as well as a sensor on the torso to monitor movement in the user's center of gravity. A pulse detector to monitor heart rate could be added to any one of the sensors.

The sensor 10 converts the measured parameter to a signal which is transmitted via an infrared link 12 to a monitor 14. The monitor 14 uses the measured parameter to determine the level of physiological exertion and displays one or more indications of the exertion level. In the illustrated example, the monitor 14 is displaying the heart rate 18 and the equivalent running speed 16 of the user 8. Other indications of the exertion level that might be displayed include the rate of exertion in watts or horsepower or calories burned per minute or per hour. In this example, the monitor 14 also includes a video display 20 which is showing a panoramic scene to entertain and inspire the user 8 while exercising.

Figure 2:
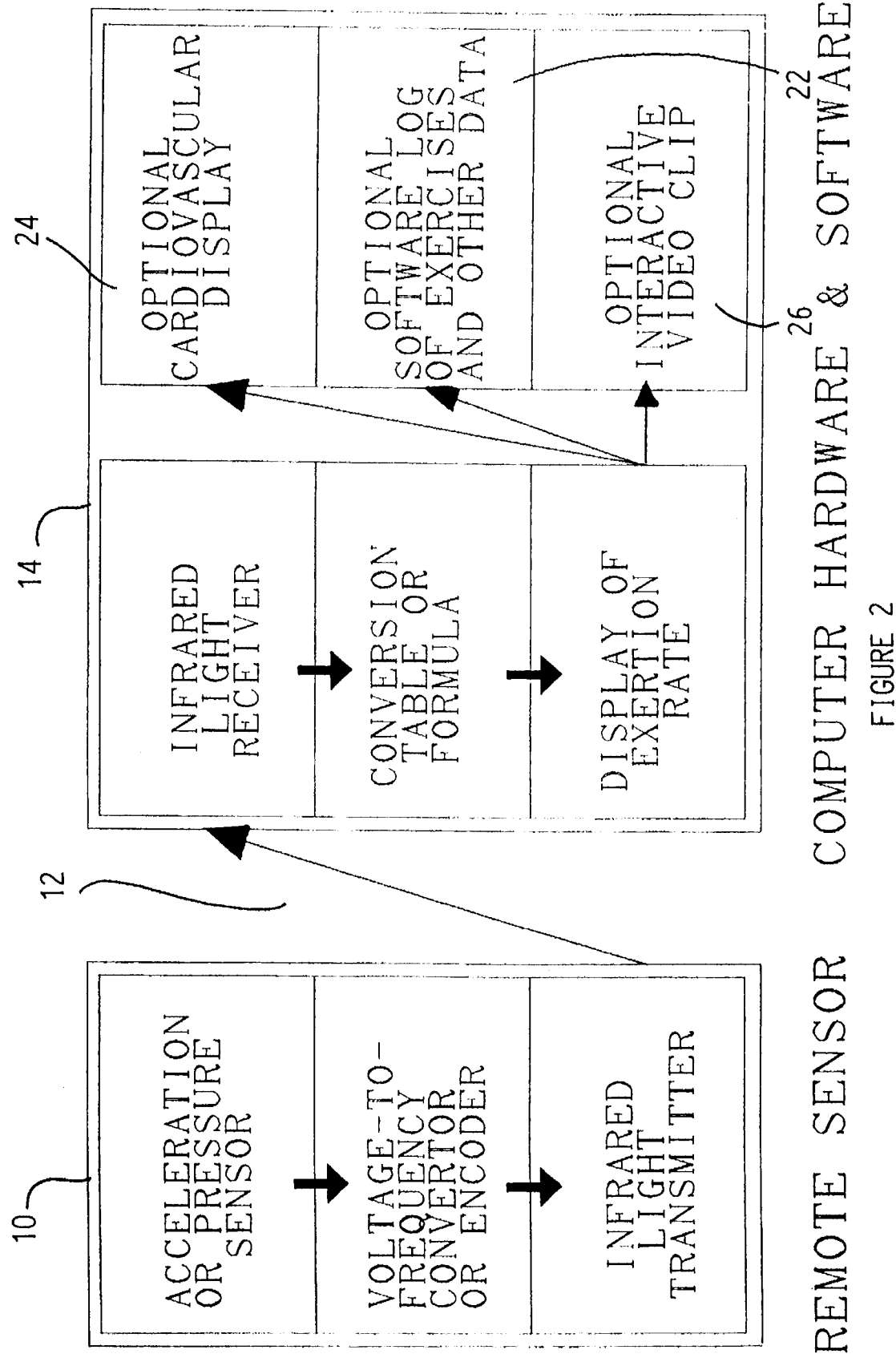
FIG. 2 is a block diagram of the monitoring system, designed in accordance with the principles of the present invention.

FIG. 2 shows the monitoring system in schematic or block diagram form. The monitoring system may provide information on the acceleration of or pressure exerted by the body or limbs, in one or more directions. In addition, if desired, the pulse or other cardiovascular parameters could be monitored and recorded.

The associated software would comprise an algorithm (expressed as a look-up table, matrix, formula, or decision flowchart) to estimate exertion from the acceleration data and pertinent individual information. Additional features might include a means to estimate cardiovascular fitness, a record of past measurements and completed exercises, and a menu of video clips.

The steps of the block diagram in FIG. 2 are labeled with the reference numbers of the corresponding components of the system from FIG. 1. The remote sensor 10 measures a parameter, such as acceleration, force, pulse rate, etc. The sensor generally expresses the measured parameter as an analog voltage signal. The sensor 10 coverts or encodes the analog voltage signal to a signal more easily transmitted, such as a frequency modulated signal. The sensor 10 transmits the encoded signal via the infrared link 12 to the monitor 14. The monitor 14 receives the signal and uses the measured parameter(s) to calculate or estimate the level of physiological exertion using a formula or a conversion table. The monitor 14 displays the exertion rate of the user. Optionally, the monitor 14 can also be used to display cardiovascular data 24, a personal exercise log 22 or an interactive video clip 26. These optional displays are illustrated graphically in FIG. 4.

Figure 3:
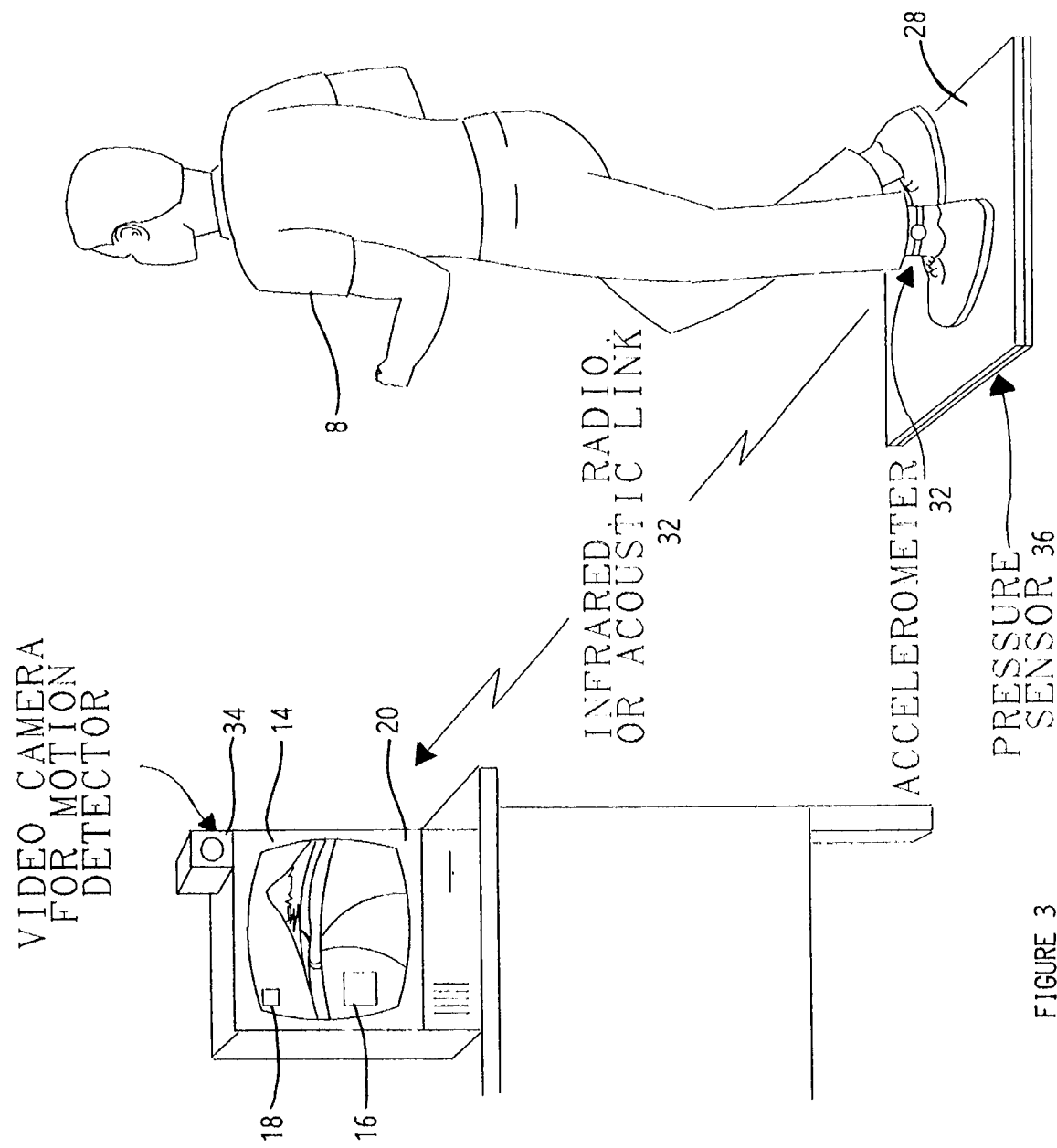
FIG. 3 illustrates different means for monitoring the exertion level.

FIG. 3 illustrates different means for monitoring and communicating the level of exertion. The use of miniature accelerometers and pressure sensors appears to provide a very accurate, inexpensive, and flexible method of monitoring limb or body motion and exertion. For similar reasons infrared light seems to be a widely accepted and economical wireless communication mode. However, other means exist to achieve both the measurement of exertion and the communication, and it is not presently possible to predict which method will be cheapest, most reliable, or widely acceptable in the future.

In this illustrative embodiment, the remote sensors include an accelerometer 30 attached to the ankle of the user 8 and a pad 28 with a built in pressure sensor 36. The accelerometer 30 and the pressure sensor 36 convert their measured parameters to a transmission signal which is transmitted to the monitor 14 by way of a wireless communication link 32, such as an infrared, acoustic or radio transmitter. A video camera 34 is illustrated as another means for monitoring the motion of the user 8. The video camera 34 can be used to monitor body and limb motion, and the amplitude and the frequency or rate of body and limb motion could then be easily determined by evaluating individual pixels, applying any one of a number of algorithms such as edge detection, Fourier analysis, or best-fit criteria using simulations with one or more independent parameters. The amplitude and rate of body and limb motion can then be used to determine the rate of physiological exertion of the user. Visually distinct markers can be attached to the user to more clearly delineate the user's motion, thereby enhancing the ability of the video camera system to detect and analyze the user's motion during exercise. For instance, one or more highly reflective markers, light-emitting diodes or other markers can be strapped to the user's body, feet or hands to more clearly delineate the motion.

Figure 4:
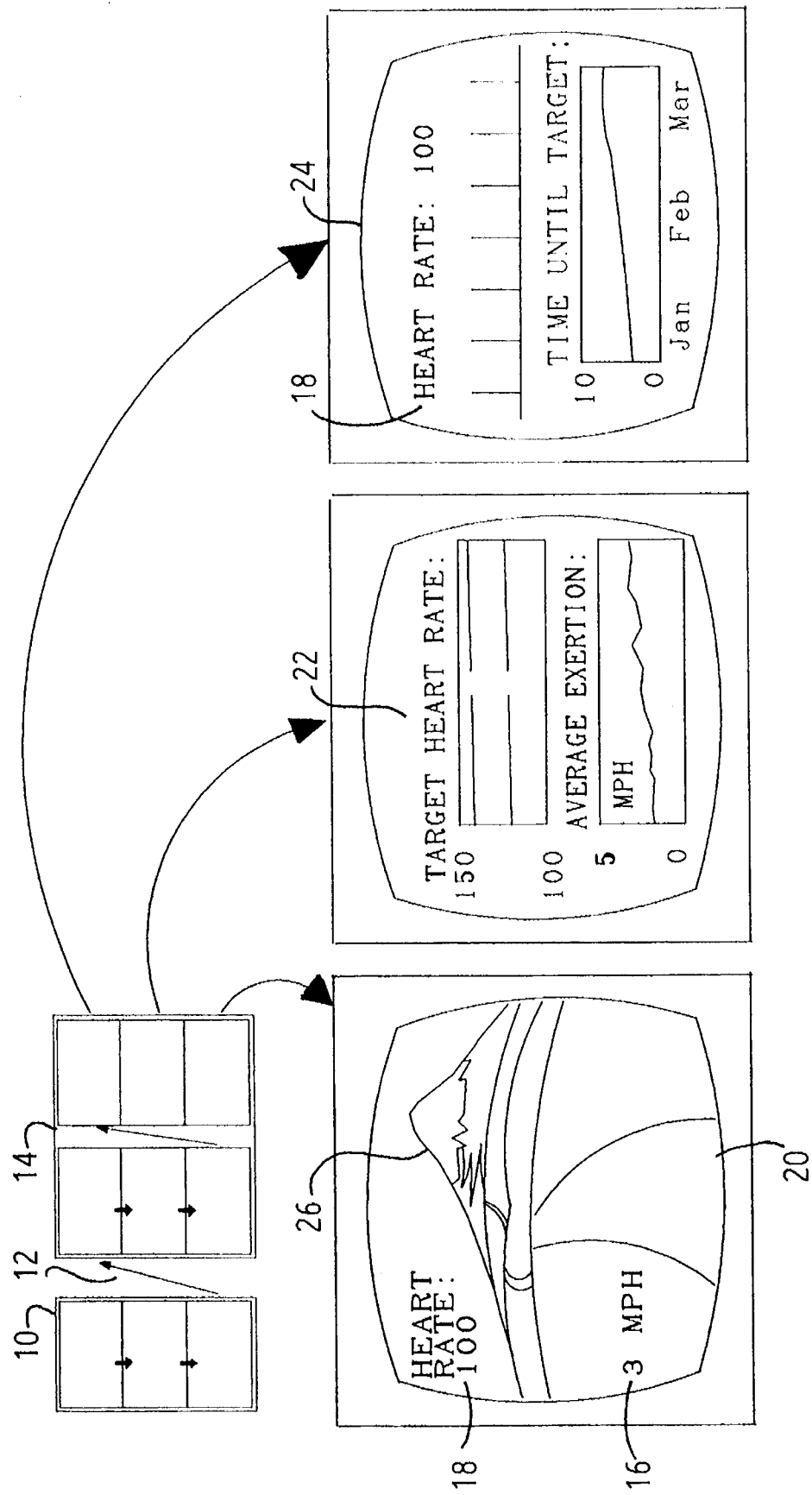
FIG. 4 illustrates the computer displays that might be associated with an optional cardiovascular data monitoring algorithm, interactive video system, and a personal exercise log which can be kept in software form.

FIG. 4 illustrates various optional arrangements such as an automated cardiovascular data entry 24, an interactive video system 26, and a personal exercise log 22 which can be kept in a software record.

The cardiovascular monitoring algorithm would record and if desired display heart rate 18, along with the target range for the individual and exercise program. A visual or auditory warning could be given if the heart beat were too fast or irregular.

The interactive video system 26 displays scenery or other inspirational images on the video display 20. The scenery displayed in a video sequence may be in the form of a "story" with several alternative episodes at certain branch points. For example, one might choose an alpine travelogue from a video menu that also included such fare as a walking tour of the pyramids of Egypt, the temples of Angkor Wat, and a Moon walk. The scenery in such an alpine video clip could be taken along a roadway ascending through hills into the Alpine mountains. Such video clips can now be stored and accessed relatively inexpensively, due to the availability of mass storage devices such as optical disks. Another option may be to create a simulated landscape, calculated using the equations for geometric solids and fractals. This, or a combination of real and simulated landscapes, would permit limitless branch-points in a given video sequence.

Past cardiovascular measurements and completed exercises are entered into a software log or spreadsheet. This data can be charted or displayed 22 in order to assess progress in an exercise regimen, and reasonable future goals for improvement.

A projection television system can be used if desired, for example in a spa, health club, or group exercise program. Individual accelerometers or pressure sensors may be uniquely identified in the communication protocol if desired, and sufficient bandwidth exists in any of the communication systems mentioned to handle the transfer of information between many individuals and a single computer station. Likewise, members of such a group could record their performance privately, or publicly such as for purposes of competition with appropriate handicaps analogous to those used in the game of golf.

Ramifications and Scope

Perhaps the most practical application of the invention in terms of economic value, would be to offer an inexpensive alternative to mechanical treadmills such as are presently used in physician's offices. Such a system may cost in excess of $10,000 plus about $1000 each year for floor rent, maintenance, and electrical utilities. In contrast, the present invention takes up virtually no space on a permanent basis, and requires little maintenance or electrical power. Physicians are compensated by most health insurance programs in the United States of America on the basis of procedures for which standardized codes exist. The fees for a given procedure are determined somewhat arbitrarily, but in part by the costs of the associated equipment. Thus, if rendered sufficiently accurate by the development of a detailed table or formula, the present invention could dramatically lower the costs of one well-established medical procedure: a cardiovascular examination involving the use of a mechanical treadmill typically costs $150–$200, but probably would only cost about $75–100 if the equipment costs were minimal (e.g. less than $1000).

However, the acceptance of such an invention by private physicians and by health maintenance organizations (HMOs) depends only in part on its accuracy, reproducibility, and ease of use. Other intangible social and cultural expectations also exist, with respect to the appearance and presentation of medical technology. It is probable that these expectations can be entirely satisfied by means of the cardiovascular monitoring and interactive video options. The present system potentially provides a more accurate measure of exertion than is possible on a treadmill, since it can be rendered independent of gait and may be used to estimate the actual work performed by the individual.

Other applications exist for home or business use such as interactive entertainment, personal fitness, and physical training programs. Many programs for physical training presently use expensive equipment such as mechanical treadmills and stationary bicycles. Most of the corresponding motions and exertions can actually be simulated without the use of mechanical devices, and the chief purpose of the equipment is to provide a consistent and accurate measure of exertion. While cultural barriers may exist to the adoption of such a "virtual reality" physical training program, such barriers are less likely to exist in other countries in which calisthenics are already in widespread use.

Educational, training, and entertainment applications.

Educational applications can be devised by means of video clips or appropriate software. This includes learning about one's own physiological parameters and fitness, or experiencing in an interactive fashion the results of normal exertion on the surface of the Moon or other extraterrestrial environments.

Training applications also exist, such as for mountain climbers or spelunkers (cave explorers) planning an expedition and wishing to become intimately familiar with the route. (It is common practice for mountain climbers to train physically for a given ascent, often for weeks or months.) With additional sensors to monitor limb and body motion and exertion, it should be possible to devise interactive software tutorial programs in dance, martial arts, and other physical activities. The extension of such training applications to include the use of such sports equipment as baseball bats, tennis rackets, and so forth is considered obvious.

Entertainment applications can also be created by means of video clips, in the form of narrative travelogues or games for one or more players.

Wellness and health maintenance programs.

The advantages of regular physical activity are well-known among all age groups. While group exercise programs are often implemented in retirement communities and resort settings, these are more difficult to organize and achieve in urban settings or among busy working adults. Moreover, many elderly people prefer to live at home in familiar surroundings, rather than in a retirement community. With the present invention, it would be possible to devise programs for groups of individuals in their own homes but linked by electronic communication. In such a program, a trained physical therapist or instructor could provide an exercise routine, while monitoring individual activity and (if desired) cardiovascular fitness as well. Peer-to-peer monitoring could also be implemented to provide more interaction and a sense of community or group identification.

Miscellaneous control applications.

Possible telemetry applications include the control of remote devices. Measurement of fine gradations of exertion on the part of an operator may be useful in calibrating the skillful and delicate operation of remote or prosthetic devices. The present system requires a minimum of equipment for measurement of operator motion or exertion, and does not encumber the natural movements of the body.

While it is likely that special purpose sensors and training programs would actually be required for commercial and industrial applications, some consumer electronic applications may exist for which the present system is well-suited (e.g. remote-control lawnmowers, toy robots, radio-controlled airplanes and boats, and so on).

Although the illustrative embodiments show several examples of this invention, it is to be understood that various modifications and substitutions for the illustrative devices, interactive video technology, and wireless communication system; for the computer hardware and software technology; and for the algorithm (expressed in a flowchart, formula, matrix, or table) used to estimate exertion may be made by those skilled in the relevant art without departing from the novel spirit and scope of the present invention.

What is claimed is:

1. A system for measuring physiological exertion, comprising:

at least one sensor means for sensing a motion of a user, said sensor means including a converter means for creating a signal indicative of said motion of said user and a transmitter means for transmitting said signal, and a monitor, said monitor including a receiver means for receiving said signal, a correlation means for correlating said signal indicative of said motion of said user with a level of physiological exertion of said user and display means for displaying an indication of said level of physiological exertion of said user.

2. The system of claim 1 wherein said sensor means comprises at least one accelerometer and a means for affixing said sensor means to a limb of said user.

3. The system of claim 1 wherein said sensor means comprises at least one pressure sensor for sensing a force exerted by said user.

4. The system of claim 1 wherein said sensor means comprises at least one remote optical sensor and a means for determining the rate and amplitude of said motion of said user.

5. The system of claim 4 wherein said at least one remote optical sensor comprises at least one video camera for sensing said motion of said user.

6. The system of claim 1 wherein said transmitter means comprises an infrared signal transmitter and said receiver means comprises an infrared signal receiver.

7. The system of claim 1 wherein said correlation means comprises a computer which uses a mathematical formula to calculate said level of physiological exertion of said user based on said motion of said user.

8. The system of claim 1 wherein said correlation means comprises a computer which estimates said level of physiological exertion of said user by use of a look up table which correlates said motion of said user to a level of physiological exertion of said user.

9. The system of claim 1 further comprising an interactive video display means, said interactive video display means displaying an image having at least one image parameter which is controlled interactively dependent on said signal indicative of said motion of said user.

10. The system of claim 9 wherein said interactive video display means displays an image of scenery and said at least one image parameter which is controlled interactively dependent on said signal indicative of said motion of said user includes movement of said scenery in said image at a rate corresponding with said level of physiological exertion of said user.

11. The system of claim 9 wherein said interactive video display means displays an image of scenery and said at least one image parameter which is controlled interactively dependent on said signal indicative of said motion of said user includes movement of said scenery in said image in a direction corresponding with a movement of said user sensed by said sensor means.

12. The system of claim 9 wherein said interactive video display means includes a recording of a branching video sequence, said branching video sequence having a multiplicity of branch points at which said branching video sequence can take a plurality different directions and wherein the direction taken at each of said multiplicity of branch points in said branching video sequence is controlled interactively dependent on said signal indicative of said motion of said user.

13. The system of claim 1 further comprising a means for measuring at least one physiological parameter of said user.

14. The system of claim 13 wherein said means for measuring at least one physiological parameter of said user measures the pulse rate of said user.

15. The system of claim 13 wherein said means for measuring at least one physiological parameter of said user measures the blood pressure of said user.

16. The system of claim 1 further comprising a memory means for recording said level of physiological exertion of said user.

17. The system of claim 16 wherein said memory means records said level of physiological exertion of said user as a function of time, whereby said user can monitor the progress of a physical training program over time.

18. The system of claim 1 wherein said correlation means correlates said signal indicative of said motion of said user with a metabolic rate of said user and said display means displays an indication of said metabolic rate of said user.

19. The system of claim 18 further comprising a calculation means for calculating a total energy expended by said user over a period of time based on said signal indicative of said motion of said user and wherein said display means displays an indication of said total energy expended.

20. The system of claim 1 further comprising a calculation means for calculating a total energy expended by said user over a period of time based on said signal indicative of said motion of said user and wherein said display means displays an indication of said total energy expended.

21. A system for measuring physiological exertion, comprising:

at least one sensor means and a means for affixing said sensor means to a limb of said user, said sensor means comprising at least one accelerometer for sensing a motion said limb of said user and a means for measuring at least one physiological parameter of said user, said sensor means further including a converter means for creating a signal indicative of said motion said limb of said user and said at least one physiological parameter of said user, and an infrared signal transmitter for transmitting said signal, a monitor, said monitor including an infrared signal receiver for receiving said signal, a computer for correlating said signal with a level of physiological exertion of said user and display means for displaying an indication of said level of physiological exertion of said user and for displaying an indication of said at least one physiological parameter of said user, an interactive video display means, said interactive video display means displaying an image having at least one image parameter which is controlled interactively dependent on said signal, and a memory means for recording said level of physiological exertion of said user and said at least one physiological parameter of said user as a function of time, whereby said user can monitor the progress of a physical training program over time.

22. The system of claim 21 wherein said interactive video display means includes a recording of a branching video sequence, said branching video sequence having a multiplicity of branch points at which said branching video sequence can take a plurality different directions and wherein the direction taken at each of said multiplicity of branch points in said branching video sequence is controlled interactively dependent on said signal.

\* \* \* \* \*